US012576255B2

(12) United States Patent
Sharma

(10) Patent No.: US 12,576,255 B2
(45) Date of Patent: Mar. 17, 2026

(54) ADJUSTABLE SEAL

(71) Applicant: BOSTON SCIENTIFIC MEDICAL DEVICE LIMITED, Galway (IE)

(72) Inventor: Deepak Kumar Sharma, Muzaffarnagar (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 680 days.

(21) Appl. No.: 18/096,603

(22) Filed: Jan. 13, 2023

(65) Prior Publication Data

US 2023/0218878 A1 Jul. 13, 2023

Related U.S. Application Data

(60) Provisional application No. 63/299,189, filed on Jan. 13, 2022.

(51) Int. Cl.
A61M 39/06 (2006.01)

(52) U.S. Cl.
CPC . A61M 39/0613 (2013.01); A61M 2039/0673 (2013.01); A61M 2039/0686 (2013.01)

(58) Field of Classification Search
CPC ... A61M 5/344; A61M 5/345; A61M 39/0613
See application file for complete search history.

(56) References Cited

U.S. PATENT DOCUMENTS

| | | | | |
|---|---|---|---|---|
| 1,526,824 | A | * | 2/1925 | Bock ..................... A61M 5/344 604/243 |
| 3,063,450 | A | | 11/1962 | Simon et al. |

| | | | | |
|---|---|---|---|---|
| 5,348,317 | A | * | 9/1994 | Steadings ........... B23B 31/1238 279/62 |
| 5,350,101 | A | * | 9/1994 | Godlewski ............. B65H 51/18 226/161 |
| 5,935,112 | A | | 8/1999 | Stevens et al. |
| 8,945,059 | B2 | | 2/2015 | Loewen |
| 8,968,249 | B2 | | 3/2015 | Smith et al. |
| 2005/0020981 | A1 | * | 1/2005 | Kurth ................ A61M 39/0613 604/167.06 |

(Continued)

FOREIGN PATENT DOCUMENTS

| | | | | |
|---|---|---|---|---|
| CN | 208895254 | U | * | 5/2019 |
| JP | H07241339 | A | | 9/1995 |

OTHER PUBLICATIONS

International Search Report and Written Opinion dated Mar. 30, 2023 for International Application No. PCT/US2023/010733.

*Primary Examiner* — William R Carpenter
(74) *Attorney, Agent, or Firm* — Seager, Tufte & Wickhem, LLP

(57) ABSTRACT

A medical device is adapted to seal around elongate shafts of varying diameter therethrough. The medical device includes a plurality of elastomeric sealing members together defining a variable dimension aperture, a chuck body, and a chuck ring that is rotatably secured relative to the chuck body. The medical device is adapted such that rotating the chuck ring in a first direction causes the plurality of elastomeric sealing members to move closer together, thereby reducing a size of the variable dimension aperture, and rotating the chuck ring in a second direction causes the plurality of elastomeric sealing members to move farther apart, thereby increasing a size of the variable dimension aperture.

19 Claims, 9 Drawing Sheets

(56) References Cited

U.S. PATENT DOCUMENTS

| | | | |
|---|---|---|---|
| 2005/0090779 A1* | 4/2005 | Osypka | A61M 25/0662 |
| | | | 604/160 |
| 2009/0115144 A1* | 5/2009 | Gong | B23B 31/1238 |
| | | | 279/62 |
| 2013/0138086 A1* | 5/2013 | Thor | A61M 25/0014 |
| | | | 604/535 |
| 2016/0175564 A1* | 6/2016 | Eberle | A61M 39/0613 |
| | | | 604/528 |
| 2021/0023336 A1 | 1/2021 | Lee | |

* cited by examiner

ADJUSTABLE SEAL

CROSS-REFERENCE TO RELATED APPLICATIONS

This application claims the benefit of priority under 35 U.S.C. § 119 of U.S. Provisional Application No 63/299,189, filed Jan. 13, 2022 the entire disclosure of which is hereby incorporated by reference.

TECHNICAL FIELD

The present disclosure pertains to medical devices, and methods for manufacturing and using medical devices. More particularly, the disclosure is directed to an adjustable seal.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, an adjustable seal is adapted to accommodate elongate medical devices of varying diameter therethrough. The adjustable seal includes an inner chuck body having a longitudinal axis and a plurality of threaded rods extending through the inner chuck body at an acute angle with respect to the longitudinal axis. An outer chuck ring is rotatably secured relative to the inner chuck body. An inner chuck ring includes a threaded surface adapted to threadedly engage with the plurality of threaded rods, the inner chuck ring secured to the outer chuck ring such that rotation of the outer chuck ring causes the inner chuck ring to rotate relative to the plurality of threaded rods. The adjustable seal includes a plurality of elastomeric sealing members, with one of the plurality of elastomeric sealing member secured to each of the plurality of threaded rods, such that the elastomeric sealing members together define a variable dimension aperture that changes size as the plurality of threaded rods translate relative to the inner chuck ring.

Additionally or alternatively, the adjustable seal may be adapted such that rotating the outer chuck ring in a first direction causes the plurality of elastomeric sealing members to move closer together, thereby reducing a size of the variable dimension aperture defined by the plurality of elastomeric sealing members.

Additionally or alternatively, the adjustable seal may be adapted such that rotating the outer chuck ring in a second direction causes the plurality of elastomeric sealing members to move farther apart, thereby increasing a size of the variable dimension aperture defined by the plurality of elastomeric sealing members.

Additionally or alternatively, the inner chuck body may define a plurality of angled apertures that extend through the inner chuck body.

Additionally or alternatively, the plurality of angled apertures may be adapted to allow the plurality of threaded rods to translate within the plurality of angled apertures.

Additionally or alternatively, the threaded surface of the inner chuck ring may be angled in order to match the acute angle with respect to the longitudinal axis that the plurality of threaded rods are disposed at.

Additionally or alternatively, the adjustable seal may further include a manifold portion that is adapted to be secured to another device.

Additionally or alternatively, the adjustable seal may further include a shaft portion extending from the manifold portion, the shaft portion adapted to be secured to another device.

Additionally or alternatively, the adjustable seal may further include an indicator display that provides an indication of a current dimension of the variable dimension aperture.

Additionally or alternatively, each of the plurality of elastomeric members may include a plurality of elastomeric layers, with each elastomeric layer secured to an adjoining elastomeric layer rotated relative to the adjoining elastomeric layer.

Additionally or alternatively, the variable dimension aperture defined by the plurality of elastomeric members may be adapted to seal against a guidewire.

Additionally or alternatively, the variable dimension aperture defined by the plurality of elastomeric members may be adapted to seal against a dilator sheath as large as 22 French (F).

As another example, a medical device is adapted to accommodate elongate shafts of varying diameter therethrough. The medical device includes an inner chuck body and a plurality of threaded rods that extend through the inner chuck body. A chuck ring is rotatably secured relative to the inner chuck body and is adapted to threadedly engage with the plurality of threaded rods such that rotation of the chuck ring causes the plurality of threaded rods to translate in response. An elastomeric sealing assembly defines a variable dimension sealing aperture that is adapted to change size as the plurality of threaded rods translate relative to the inner chuck ring.

Additionally or alternatively, the elastomeric sealing assembly may include a plurality of elastomeric sealing members, with one of the plurality of elastomeric sealing member secured to each of the plurality of threaded rods, such that the elastomeric sealing members together define the variable dimension aperture.

Additionally or alternatively, each of the plurality of elastomeric members may include a plurality of elastomeric layers, with each elastomeric layer secured to an adjoining elastomeric layer rotated relative to the adjoining elastomeric layer.

Additionally or alternatively, the chuck ring may include an outer chuck ring rotatably secured relative to the inner chuck body, and an inner chuck ring including a threaded surface adapted to threadedly engage with the plurality of threaded rods, the inner chuck ring secured to the outer chuck ring such that rotation of the outer chuck ring causes the inner chuck ring to rotate.

As another example, a medical device is adapted to accommodate elongate shafts of varying diameter therethrough. The medical device includes a plurality of elastomeric sealing members together defining a variable dimension aperture, a chuck body, and a chuck ring rotatably secured relative to the chuck body. The medical device is adapted such that rotating the chuck ring in a first direction causes the plurality of elastomeric sealing members to move closer together, thereby reducing a size of the variable dimension aperture, and rotating the chuck ring in a second direction causes the plurality of elastomeric sealing members to move farther apart, thereby increasing a size of the variable dimension aperture.

Additionally or alternatively, the medical device may further include a plurality of threaded rods slidingly disposed within the chuck body, the plurality of threaded rods adapted to threadedly engage the chuck ring such that rotation of the chuck ring causes the plurality of threaded rods to translate. The plurality of elastomeric sealing members are secured relative to the plurality of threaded rods such that the plurality of elastomeric sealing members move relative to each other as the plurality of threaded rods translate relative to the chuck body.

Additionally or alternatively, each of the plurality of elastomeric members may include a plurality of elastomeric layers, with each elastomeric layer secured to an adjoining elastomeric layer rotated relative to the adjoining elastomeric layer.

Additionally or alternatively, the chuck ring may include an outer chuck ring rotatably secured relative to the inner chuck body and an inner chuck ring including a threaded surface adapted to threadedly engage with the plurality of threaded rods, the inner chuck ring secured to the outer chuck ring such that rotation of the outer chuck ring causes the inner chuck ring to rotate.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
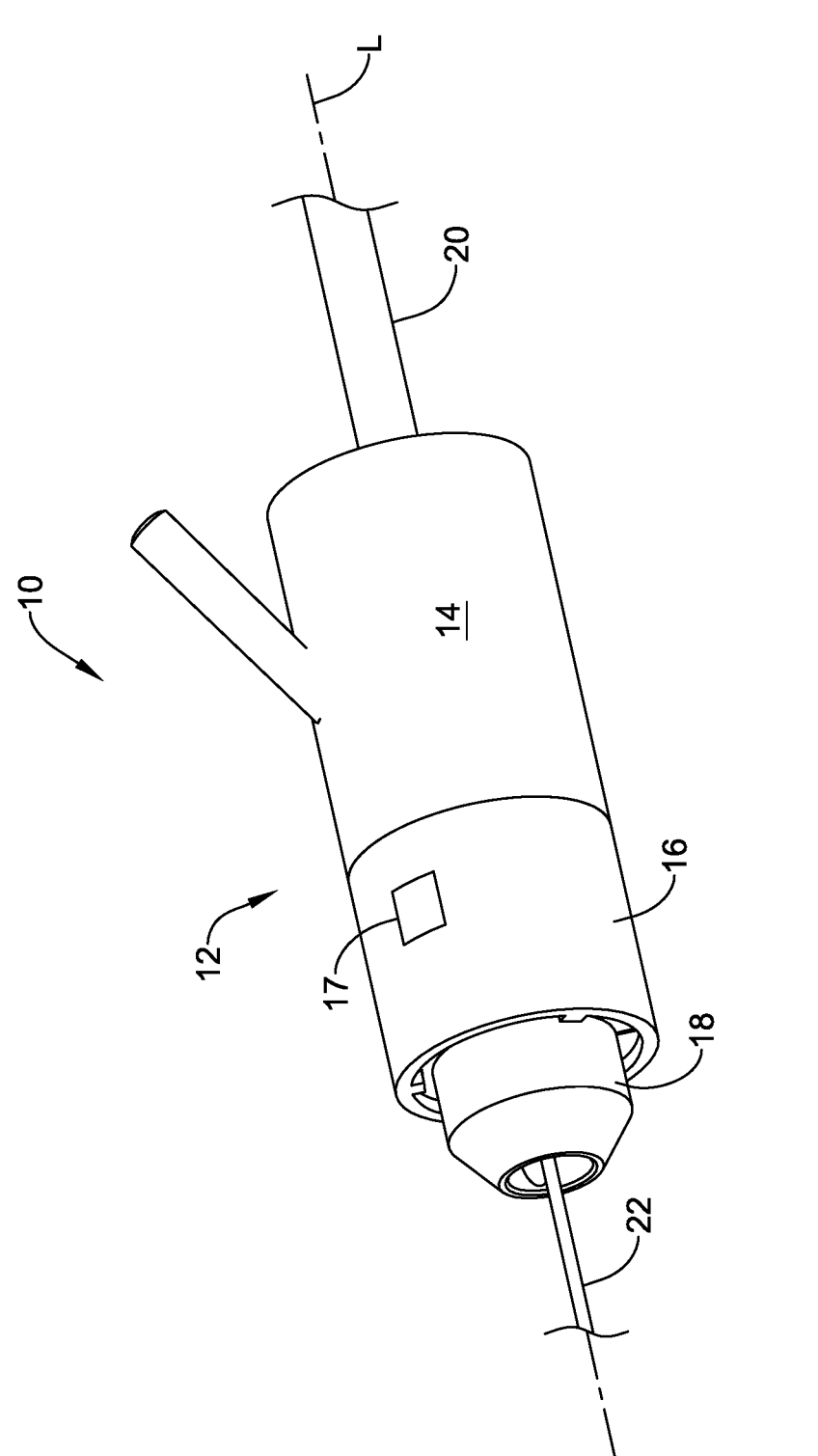
FIG. 1 is a perspective view of an illustrative adjustable seal.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

A variety of different medical devices, including but not limited to guidewires, catheters, dilation catheters and the like, are frequently passed through seals that allow the different medical devices to pass through a device while reducing or even eliminating possible fluid flow through the seal. In some cases, there may be a desire to be able to pass medical devices having substantially different diameters through a common seal, without the common seal leaking. For example, there may be a desire to pass a relatively small medical device such as a guidewire through a seal and also pass a relatively large medical device such as a catheter or a dilator through the seal. In some cases, the relatively large medical device may be advanced over the guidewire.

FIG. 1 is a perspective view of an illustrative adjustable seal 10 that is adapted to permit a variety of different-sized medical devices to pass through the adjustable seal 10 while not permitting fluid leakage around the different-sized medical devices that extend through the adjustable seal. The adjustable seal 10 includes a body 12. In some cases, the body 12 may include a manifold 14 and an outer chuck ring 16. As will be discussed, rotating the outer chuck ring 16 causes the adjustable seal 10 to accommodate either a smaller-diameter medical device or a larger-diameter medical device therethrough, without leakage, depending on which direction the outer chuck ring 16 is rotated relative to the rest of the body 12. The adjustable seal 10 includes a longitudinal axis L, which in some cases may indicate a relative orientation of any medical device extending through the adjustable seal 10.

The adjustable seal 10 includes an inner chuck body 18 that extends distally from the outer chuck ring 16. Details of how rotation of the outer chuck ring 16 enables the adjustable seal 10 to accommodate a variety of differently sized medical devices will be discussed with respect to subsequent Figures. A proximal shaft 20 extends from the manifold 14, and may be used as a catheter in any of a variety of different procedures, such as but not limited to mechanical thrombectomy for aspiration of thrombus and delivering stents for percutaneous coronary intervention. It will be appreciated that the stiff shaft 20 provides stiffness and support for navigating through the anatomy in order to deliver therapy. The adjustable seal 10 and the proximal shaft 20 may be adapted for use in GI (gastrointestinal) procedures that include the use of an endoscope, for example. As shown, a catheter 22 extends distally through the adjustable seal 10.

Figure 2:
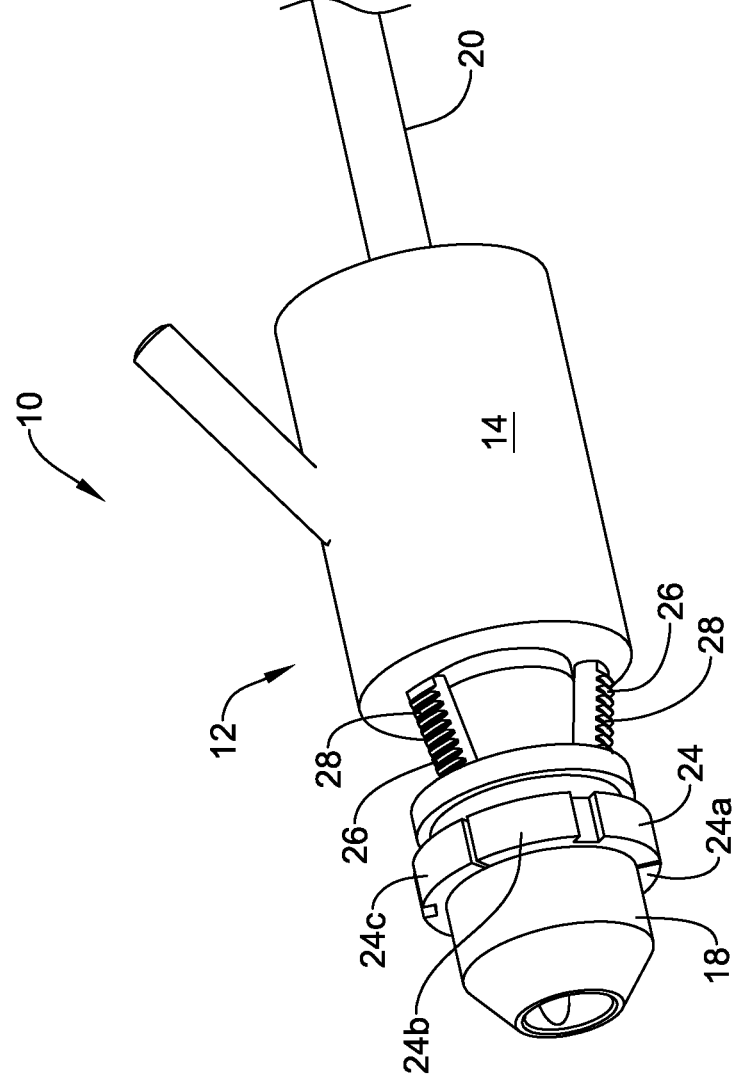
FIG. 2 is a perspective view of the illustrative adjustable seal of FIG. 1, with components removed to show internal structure.

In some cases, the adjustable seal 10 may include an index 17 that provides an indication of what size medical device the adjustable seal 10 is currently configured to accommodate. The index 17 may change what is displayed as the outer chuck ring 16 is rotated. In some cases, the index 17 may simply be a window formed within the outer chuck ring 16, exposing various numbers that may be printed underneath the outer chuck ring 16 (such as on an outer surface of the inner chuck ring 24 (FIG. 2). In some cases, the index 17 may be an alphanumeric display that changes as the outer chuck ring 16 is rotated. The index 17 may display a numerical diameter, for example, or perhaps words such as "guidewire", "catheter", "dilator" and so on.

In FIG. 2, the outer chuck ring 16 has been removed in order to show portions of the structure underneath the outer chuck ring 16. An inner chuck ring 24 is rotatably disposed about the inner chuck body 18. In some cases, the inner chuck ring 24 may be formed in multiple pieces in order to facilitate assembly. As shown, the inner chuck ring 24 includes a total of three inner chuck ring components 24*a*, 24*b* and 24*c*. In some cases, the inner chuck ring 24 is securable within the outer chuck ring 16 such that the inner chuck ring 24 rotates when a user rotates the outer chuck ring 16. In some cases, the inner chuck ring 24 and the outer chuck ring 16 may, in combination, be referred to simply as a chuck ring. Rotation of the chuck ring can cause the adjustable seal 10 to change what diameter medical device it is configured to accommodate.

The adjustable seal 10 includes several threaded rods 26. In some cases, the adjustable seal 10 includes a total of three threaded rods 26, although only two are visible in FIG. 2. In some cases, the threaded rods 26 are equally circumferentially spaced about the inner chuck body 18. As will be shown with respect to FIG. 7, an inner surface of the inner chuck ring 24 is threaded in order to threadedly engage a threaded surface 28 that is formed on each of the threaded rods 26. The threaded rods 26 extend through apertures formed within the inner chuck body 18 (best seen in FIGS. 4A and 4B). As the inner chuck ring 24 is rotated (in response to being coupled with the outer chuck ring 16), the threaded engagement between the threaded inner surface of the inner chuck ring 24 and the threaded surface 28 formed on each of the threaded rods 26, the threaded rods 26 are caused to translate through the aforementioned apertures formed within the inner chuck body 18. It will be appreciated that rotating the inner chuck ring 24 in one direction will cause the threaded rods 26 to translate towards the left (in the illustrated orientation) while rotating the inner chuck ring 24 in an opposing direction will cause the threaded rods 26 to translate towards the right (in the illustrated orientation).

Figure 3:
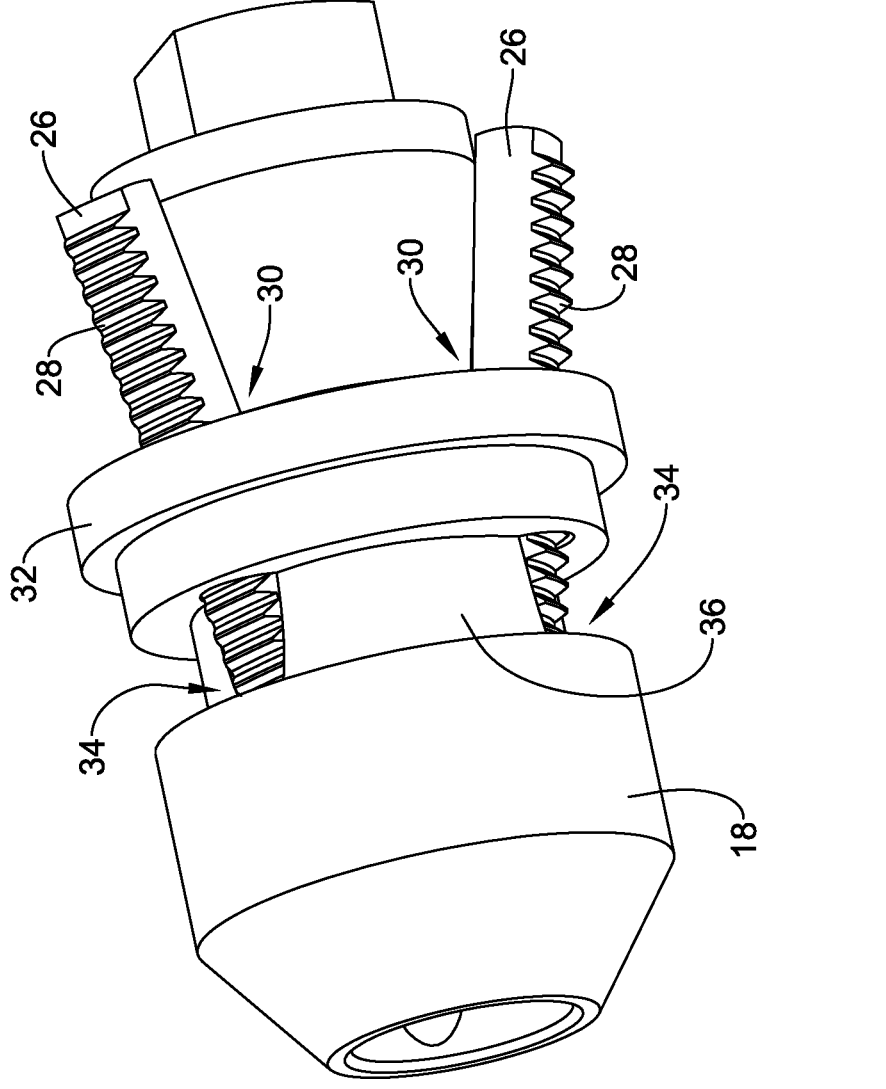
FIG. 3 is a perspective view of the illustrative adjustable seal of FIG. 1 and FIG. 2, with additional components removed to show internal structure.

In FIG. 3, the inner chuck ring 24 has been removed in order to show additional structure. It can be seen that each of the threaded rods 26 (although only two are visible here) extend through an angled aperture that extends through the inner chuck body 18. A series of three apertures 30 are formed within an annular portion 32 of the inner chuck body 18. In some cases, the three apertures 30 (only two are visible) may be equally spaced about the annular portion 32 of the inner chuck body 18. A series of three apertures 34 extend into a reduced diameter portion 36 of the inner chuck body 18. The reduced diameter portion 36 of the inner chuck body 18 corresponds to where the inner chuck ring 24 fits. It can be seen that the threaded surfaces 28 of each of the threaded rods 26 are exposed such that the threading within the inner chuck ring 24 is able to engage the threaded surfaces 28 of each of the threaded rods 26.

Figure 4A:
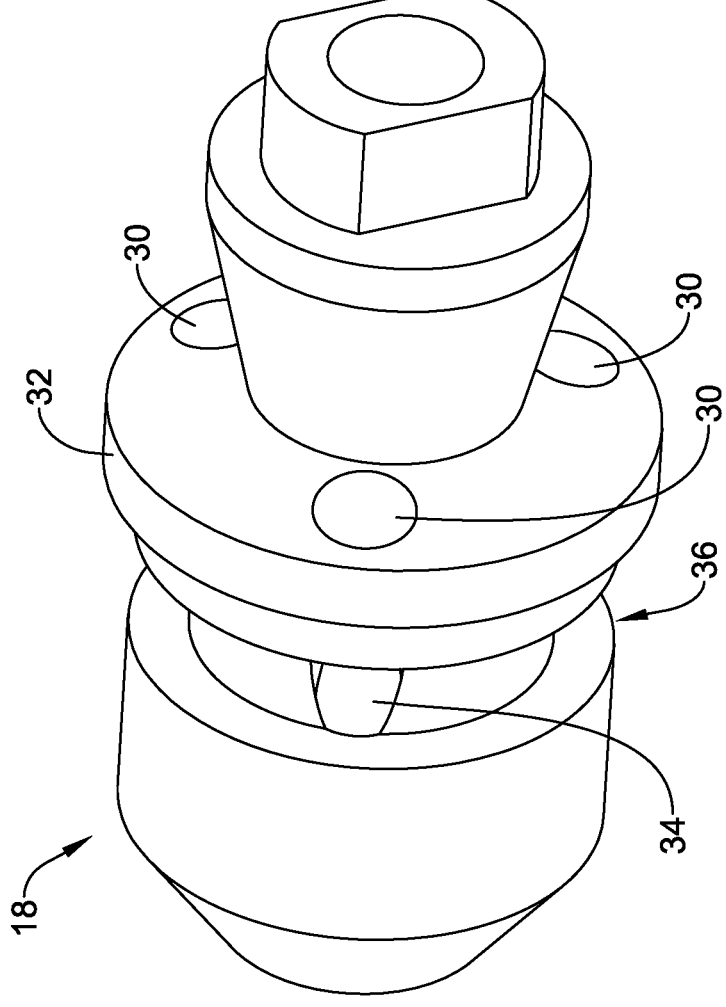
FIGS. 4A and 4B are perspective views of the chuck body forming a part of the illustrative adjustable seal of FIG. 1.
Figure 4B:
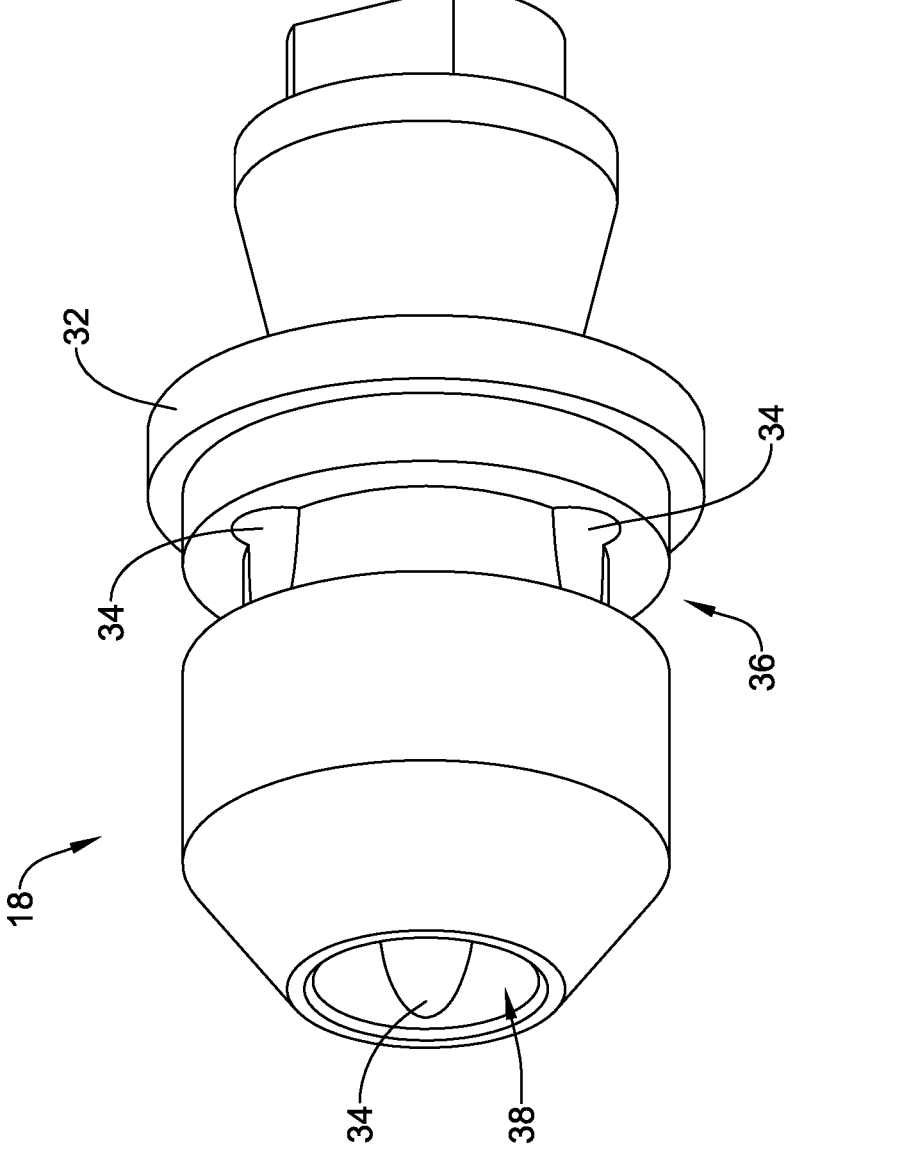

FIGS. 4A and 4B are both perspective views of the inner chuck body 18, better illustrating the apertures 30 and 34 that accommodate the threaded rods 26 therethrough. It can be seen that the apertures 34 are angled, and extend approximately to a far end (on the left, as illustrated) of the inner chuck body 18. The inner chuck body 18 includes an interior volume 38 that extends through the inner chuck body 18. The interior volume 38 not only accommodates the components that actually seal against the elongate medical devices extending through the adjustable seal 10, but also accommodates the elongate medical devices themselves.

Figure 5:
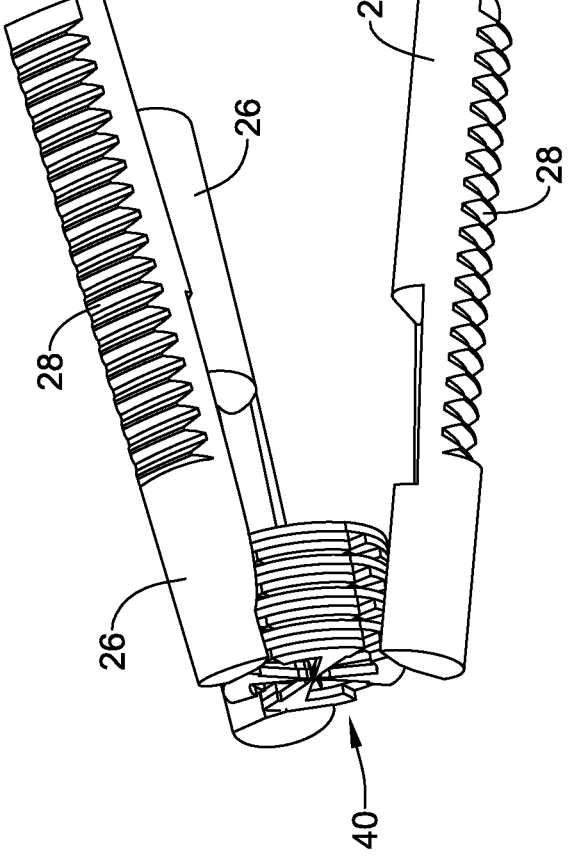
FIG. 5 is a perspective view of a portion of the illustrative adjustable seal of FIG. 1, with components removed to show internal structure.

In FIG. 5, the inner chuck body 18 has also been removed to illustrate internal structure. The three threaded rods 26, each with a threaded surface 28, can be seen. The overall orientation of the three threaded rods 26 as shown in FIG. 5 corresponds to the actual orientation of the three threaded rods 26 in the adjustable seal 10. Apart from any possible changes in the exact perspective view taken, what is seen in FIG. 5 represents what is seen in FIG. 1, simply with components removed to show internal structure.

Figures 6A, 6B:
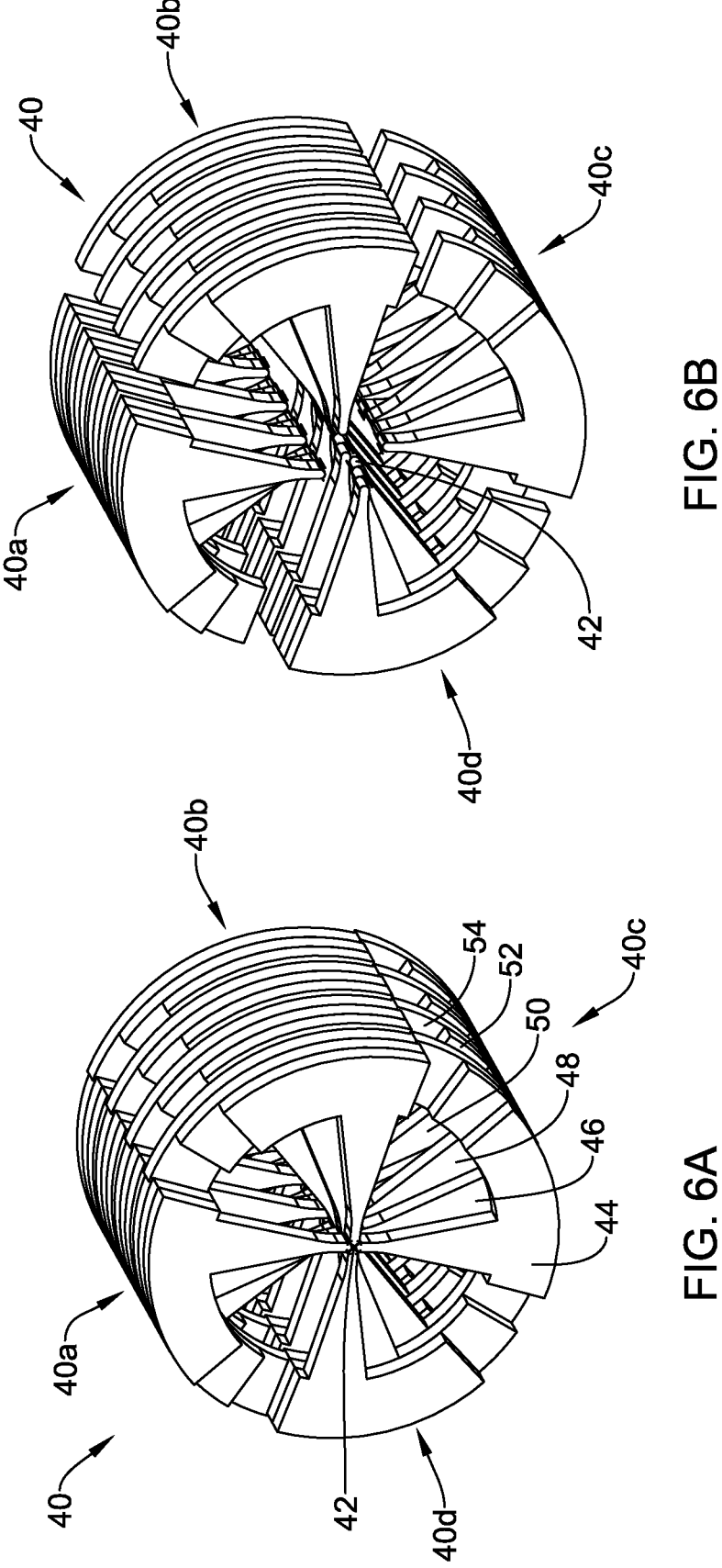
FIG. 6A is a perspective view of an elastomeric sealing assembly forming a part of the illustrative adjustable seal of FIG. 1, shown in a first configuration.
FIG. 6B is a perspective view of the elastomeric sealing assembly of FIG. 6A, shown in a second configuration.

FIG. 5 also shows an elastomeric sealing assembly 40. FIGS. 6A and 6B provide additional details regarding the elastomeric sealing assembly 40. The elastomeric sealing assembly 40, includes a number of elastomeric sealing members 40*a*, 40*b*, 40*c*, 40*d*. The elastomeric sealing members 40*a*, 40*b*, 40*c*, 40*d* are secured to the threaded rods 26, so that the elastomeric sealing members 40*a*, 40*b*, 40*c*, 40*d* move in and out relative to each other as the threaded rods 26 translate back and forth. The elastomeric sealing members 40*a*, 40*b*, 40*c*, 40*d* may be attached to the threaded rods 26 via adhesives, over-molding, sutures and the like. As the threaded rods 26 travel proximally, the elastomeric sealing members 40*a*, 40*b*, 40*c*, 40*d* travel radially and proximally.

In FIG. 6A, the elastomeric sealing members 40*a*, 40*b*, 40*c*, 40*d* are relatively closer to each other in order to provide a variable dimension aperture 42, located at a center of the elastomeric sealing assembly 40, that is adapted to seal around a small diameter medical device such as but not limited to a guidewire, for example. As an example, this configuration may occur as a result of rotating the outer chuck ring 16 in a clockwise direction, causing the threaded rods 26 to move closer to the end of the adjustable seal 10, thereby causing the attached elastomeric sealing members 40*a*, 40*b*, 40*c*, 40*d* to move closer together.

In FIG. 6B, the elastomeric sealing members 40*a*, 40*b*, 40*c*, 40*d* have moved away from each other, thereby providing the variable dimension aperture 42 with a configuration that will seal around a larger diameter medical device, such as but not limited to a catheter or a dilator. As an example, this configuration may occur as a result of rotating the outer chuck ring 16 in a counter-clockwise direction, causing the threaded rods 26 to move away from the end of the adjustable seal 10, thereby causing the attached elastomeric sealing members 40*a*, 40*b*, 40*c*, 40*d* to move farther apart.

Each of the elastomeric sealing members 40a, 40b, 40c, 40d are formed from a plurality of elastomeric layers that are secured together with each layer rotated relative to an adjacent layer. Looking at the elastomeric sealing member 40c, for example, it can be seen that the elastomeric sealing member 40c includes a first layer 44, a second layer 46 that is rotated relative to the first layer 44, a third layer 48 that is rotated relative to the second layer 46, a fourth layer 50 that is rotated relative to the third layer 48, a fifth layer 52 that is rotated relative to the fourth layer 50, a sixth layer 54 that is rotated relative to the fifth layer 52, and so on. Each of the elastomeric layers 44, 46, 48, 50, 52, 54 may be formed of any suitable elastomeric material and may be secured together using any desired technique. The elastomeric layers 44, 46, 48, 50, 52, 54 may be formed of any resilient material such as but not limited to silicone, Pebax, PTFE (poly tetra fluoroethylene) and rubber. The elastomeric layers 44, 46, 48, 50, 52, 54 may be joined together using adhesives, stapling, molding and the like.

Figure 7:
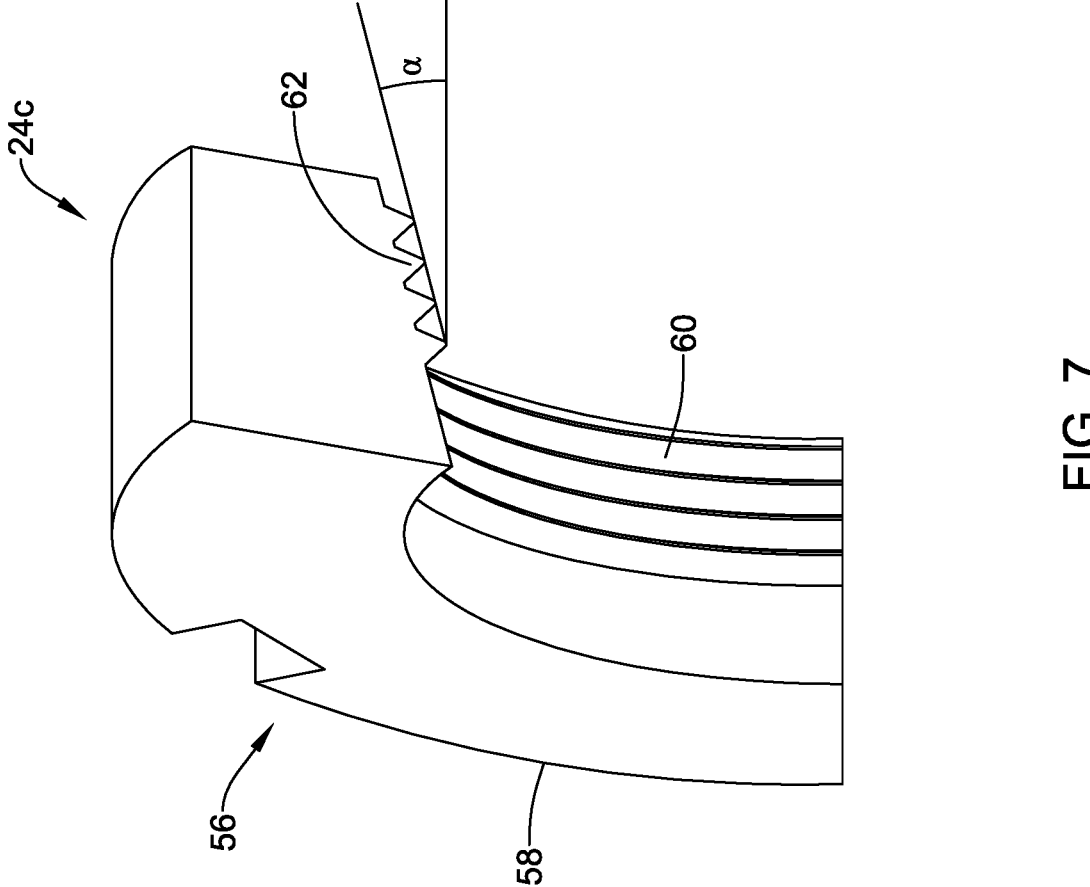
FIG. 7 is a perspective view of the illustrative adjustable seal of FIGS. 1-3, with additional components removed to show internal structure.
Figure 8:
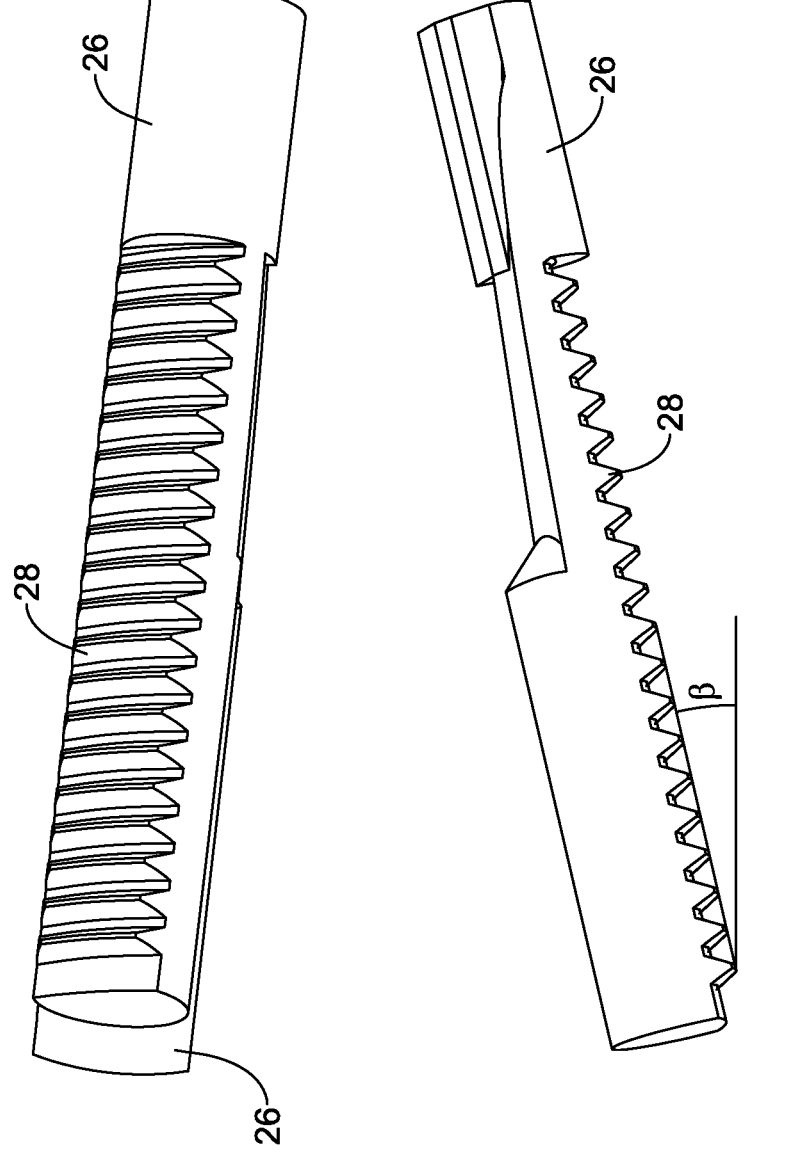
FIG. 8 is a perspective view of the illustrative adjustable seal of FIGS. 1-3, with additional components removed to show internal structure.

FIG. 7 is a perspective view of the inner chuck ring component 24c, which forms a part of the inner chuck ring 24. The inner chuck ring component 24c, like the inner chuck ring component 24a and the inner chuck ring component 24b has a partially annular body 56 (the inner chuck ring components 24a, 24b, 24c in combination form an annular shape) having an outer surface 58, which abuts an inner surface of the outer chuck ring 16, and an inner surface 60. The inner surface 60 defines a threaded surface 62 that is adapted to threadedly engage the threaded surfaces 28 formed on each of the threaded rods 26. The inner surface 60 of the inner chuck ring component 24c can be seen as forming an acute angle α (alpha) with the horizontal, which may be considered as being aligned with (or parallel with) the longitudinal axis L of the adjustable seal 10. In viewing FIG. 8, it can be seen that each of the threaded rods 26 may be considered as forming an acute angle β (beta) with the horizontal, which may be considered as being aligned with (or parallel with) the longitudinal axis L of the adjustable seal 10. In some cases, the angle α is equal to the angle β.

The adjustable seal 10, and various components thereof, may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS:

R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In addition, portions or components of the adjustable seal 10 may be coated with a relatively soft material that may improve grip such as a thermoplastic elastomer. The coating may or may not include additional features that may improve grip such as ridges, surface textures, bumps, grooves, projections, etc. Furthermore, the adjustable seal 10 disclosed herein may be designed for single use or may be designed for repeated uses. Thus, the structures disclosed herein may be manufactured from materials that can withstand multiple sterilizations and/or cleanings.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An adjustable, fluid tight seal adapted to accommodate elongate medical devices of varying diameter therethrough, the adjustable seal comprising:

an inner chuck body having a longitudinal axis;

a plurality of threaded rods extending through the inner chuck body at an acute angle with respect to the longitudinal axis; an outer chuck ring rotatably secured relative to the inner chuck body;

an inner chuck ring including a threaded surface adapted to threadedly engage with the plurality of threaded rods, the inner chuck ring secured to the outer chuck ring such that rotation of the outer chuck ring causes the inner chuck ring to rotate relative to the plurality of threaded rods; and a plurality of elastomeric sealing members, with one of the plurality of elastomeric sealing member secured to each of the plurality of threaded rods, such that the elastomeric sealing members together define a variable dimension aperture that changes size as the plurality of threaded rods translate relative to the inner chuck ring.

2. The adjustable seal of claim 1, wherein the adjustable seal is adapted such that rotating the outer chuck ring in a first direction causes the plurality of elastomeric sealing members to move closer together, thereby reducing a size of the variable dimension aperture defined by the plurality of elastomeric sealing members.

3. The adjustable seal of claim 1, wherein the adjustable seal is adapted such that rotating the outer chuck ring in a second direction causes the plurality of elastomeric sealing members to move farther apart, thereby increasing a size of the variable dimension aperture defined by the plurality of elastomeric sealing members.

4. The adjustable seal of claim 1, wherein the inner chuck body defines a plurality of angled apertures that extend through the inner chuck body.

5. The adjustable seal of claim 4, wherein the plurality of angled apertures are adapted to allow the plurality of threaded rods to translate within the plurality of angled apertures.

6. The adjustable seal of claim 1, wherein the threaded surface of the inner chuck ring is angled in order to match the acute angle with respect to the longitudinal axis that the plurality of threaded rods are disposed at.

7. The adjustable seal of claim 1, further comprising a manifold portion that is adapted to be secured to another device.

8. The adjustable seal of claim 7, further comprising a shaft portion extending from the manifold portion, the shaft portion adapted to be secured to another device.

9. The adjustable seal of claim 1, further comprising an indicator display that provides an indication of a current dimension of the variable dimension aperture.

10. The adjustable seal of claim 1, wherein each of the plurality of elastomeric members comprise a plurality of elastomeric layers, with each elastomeric layer secured to an adjoining elastomeric layer rotated relative to the adjoining elastomeric layer.

11. The adjustable seal of claim 1, wherein the variable dimension aperture defined by the plurality of elastomeric members is adapted to seal against a guidewire.

12. The adjustable seal of claim 1, wherein the variable dimension aperture defined by the plurality of elastomeric members is adapted to seal against a dilator sheath as large as 22 French (F).

13. A medical device adapted to accommodate elongate shafts of varying diameter therethrough, the medical device comprising:

an inner chuck body;

a plurality of threaded rods extending through the inner chuck body;

a chuck ring rotatably secured relative to the inner chuck body, the chuck ring adapted to threadedly engage with the plurality of threaded rods such that rotation of the chuck ring causes the plurality of threaded rods to translate in response; and an elastomeric sealing assembly defining a variable dimension sealing aperture that is adapted to change size as the plurality of threaded rods translate relative to the inner chuck ring to create a fluid tight seal about an accommodated elongate shaft.

14. The medical device of claim 13, wherein the elastomeric sealing assembly comprises a plurality of elastomeric sealing members, with one of the plurality of elastomeric sealing member secured to each of the plurality of threaded rods, such that the elastomeric sealing members together define the variable dimension aperture.

15. The medical device of claim 14, wherein each of the plurality of elastomeric members comprise a plurality of elastomeric layers, with each elastomeric layer secured to an adjoining elastomeric layer rotated relative to the adjoining elastomeric layer.

16. The medical device of claim 13, wherein the chuck ring comprises:

an outer chuck ring rotatably secured relative to the inner chuck body; and an inner chuck ring including a threaded surface adapted to threadedly engage with the plurality of threaded rods, the inner chuck ring secured to the outer chuck ring such that rotation of the outer chuck ring causes the inner chuck ring to rotate.

17. A medical device adapted to accommodate elongate shafts of varying diameter therethrough, the medical device comprising:

a plurality of elastomeric sealing members together defining a variable dimension aperture to create a fluid tight seal about an accommodated elongate shaft;

a chuck body;

a chuck ring rotatably secured relative to the chuck body;

a plurality of threaded rods slidingly disposed within the chuck body, the plurality of threaded rods adapted to threadedly engage the chuck ring such that rotation of the chuck ring causes the plurality of threaded rods to translate;

wherein the plurality of elastomeric sealing members are secured relative to the plurality of threaded rods such that the plurality of elastomeric sealing members move relative to each other as the plurality of threaded rods translate relative to the chuck body; and wherein the medical device is adapted such that rotating the chuck ring in a first direction causes the plurality of elastomeric sealing members to move closer together, thereby reducing a size of the variable dimension aperture, and rotating the chuck ring in a second direction causes the plurality of elastomeric sealing members to move farther apart, thereby increasing a size of the variable dimension aperture.

18. The medical device of claim 17, wherein each of the plurality of elastomeric members comprise a plurality of elastomeric layers, with each elastomeric layer secured to an adjoining elastomeric layer rotated relative to the adjoining elastomeric layer.

19. The medical device of claim 17, wherein the chuck ring comprises:

an outer chuck ring rotatably secured relative to the inner chuck body; and an inner chuck ring including a threaded surface adapted to threadedly engage with the plurality of threaded rods, the inner chuck ring secured to the outer chuck ring such that rotation of the outer chuck ring causes the inner chuck ring to rotate.

* * * * *